(12) United States Patent
Du et al.

(10) Patent No.: US 10,993,651 B2
(45) Date of Patent: May 4, 2021

(54) EXERCISE GUIDANCE METHOD AND EXERCISE GUIDANCE DEVICE

(71) Applicant: BOE TECHNOLOGY GROUP CO., LTD., Beijing (CN)

(72) Inventors: Hui Du, Beijing (CN); Qi Yang, Beijing (CN); Hailan Jin, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 358 days.

(21) Appl. No.: 16/022,395

(22) Filed: Jun. 28, 2018

(65) Prior Publication Data
US 2019/0046067 A1 Feb. 14, 2019

(30) Foreign Application Priority Data
Aug. 14, 2017 (CN) .......................... 201710692695.8

(51) Int. Cl.
*A61B 5/389* (2021.01)
*A63B 71/00* (2006.01)
*G16H 40/63* (2018.01)
*A61B 5/11* (2006.01)
*A61B 5/00* (2006.01)
*G16H 20/30* (2018.01)

(52) U.S. Cl.
CPC ............ *A61B 5/389* (2021.01); *A61B 5/1126* (2013.01); *A61B 5/6804* (2013.01); *A61B 5/6823* (2013.01); *A63B 71/00* (2013.01); *G16H 20/30* (2018.01); *G16H 40/63* (2018.01); *A61B 5/7203* (2013.01); *A63B 2220/80* (2013.01); *A63B 2230/08* (2013.01)

(58) Field of Classification Search
None
See application file for complete search history.

(56) References Cited

U.S. PATENT DOCUMENTS

| 2007/0167859 | A1* | 7/2007 | Finneran | ............... | A61B 5/0492 600/546 |
| 2007/0219059 | A1* | 9/2007 | Schwartz | ........... | A63B 24/0084 482/8 |
| 2008/0004904 | A1* | 1/2008 | Tran | ..................... | A61B 5/4818 705/2 |
| 2008/0071386 | A1* | 3/2008 | McBean | ............... | A61F 5/0127 623/25 |

(Continued)

FOREIGN PATENT DOCUMENTS

| CN | 101874758 A | 11/2010 |
| CN | 201894719 U | 7/2011 |
| CN | 202776300 U | 3/2013 |

OTHER PUBLICATIONS

Chinese Office Action dated Oct. 12, 2018, from application No. 201710692695.8.

*Primary Examiner* — Nathan Hillery
(74) *Attorney, Agent, or Firm* — Thomas | Horstemeyer, LLP

(57) ABSTRACT

The present disclosure provides an exercise guidance method and an exercise guidance device. The method includes receiving myoelectric parameters of a user collected by a plurality of myoelectric sensors, determining a current exercise state of the user based on myoelectric parameters, generating exercise guidance information based on the current exercise condition, and sending the exercise guidance information to a terminal.

16 Claims, 3 Drawing Sheets

(56) References Cited

U.S. PATENT DOCUMENTS

| | | | | |
|---|---|---|---|---|
| 2012/0053439 A1* | 3/2012 | Ylostalo | ............... | A61B 5/0478 |
| | | | | 600/372 |
| 2012/0123232 A1* | 5/2012 | Najarian | ................ | G16H 40/67 |
| | | | | 600/345 |
| 2012/0184871 A1* | 7/2012 | Jang | ..................... | A61B 5/1108 |
| | | | | 600/546 |
| 2015/0126826 A1* | 5/2015 | Kaleal, III | ......... | A61B 5/02055 |
| | | | | 600/301 |
| 2016/0058519 A1* | 3/2016 | Herr | ....................... | A61B 34/10 |
| | | | | 600/438 |
| 2016/0346614 A1* | 12/2016 | Kirby | ..................... | A63B 71/06 |
| 2016/0360985 A1* | 12/2016 | Ahmed | ................ | A61B 5/0082 |
| 2017/0000386 A1* | 1/2017 | Salamatian | ............. | H04L 29/06 |
| 2017/0001074 A1* | 1/2017 | Krueger | ............... | A61B 5/0531 |
| 2017/0100637 A1* | 4/2017 | Princen | ............. | G06K 9/00342 |
| 2017/0136296 A1* | 5/2017 | Barrera | ................ | A61B 5/6898 |
| 2017/0368413 A1* | 12/2017 | Shavit | ................ | G06K 9/00342 |
| 2018/0014743 A1* | 1/2018 | Fecteau | .............. | A61B 5/04087 |
| 2018/0133551 A1* | 5/2018 | Chang | ................ | A63B 24/0075 |
| 2018/0279919 A1* | 10/2018 | Bansbach | ................ | A61B 5/45 |
| 2018/0289313 A1* | 10/2018 | Inan | ....................... | A61B 7/006 |
| 2018/0330810 A1* | 11/2018 | Gamarnik | .............. | G16H 50/50 |
| 2018/0369637 A1* | 12/2018 | Hoang | .............. | G09B 19/0038 |
| 2020/0196957 A1* | 6/2020 | LeBoeuf | .............. | A61B 5/7275 |

* cited by examiner

EXERCISE GUIDANCE METHOD AND EXERCISE GUIDANCE DEVICE

CROSS REFERENCE

This application is based upon and claims priority to Chinese Patent Application No. 201710692695.8, filed on Aug. 14, 2017, the entire contents thereof are incorporated herein by reference.

TECHNICAL FIELD

The present disclosure relates to the field of computer technology, and in particular, to an exercise guidance method and an exercise guidance device.

BACKGROUND

As people pay more and more attention to their health, it presents a nationwide fitness atmosphere. During fitness, people wish to obtain information about strength and effect of the fitness.

The present guidance for fitness exercises is mainly provided by personal trainers, or a camera is used for detecting a motion posture and an image identification is applied to assist in determining whether the motion posture is correct; or otherwise an exercise monitoring device such as a health-rate belt and watch, a portable electrocardiograph and a portable oximeter having heart-rate monitoring function is used for determining exercise levels by monitoring heart-rate changes. However, on the one hand, as heart-rate changes reflect the overall exercise level without accurately reflecting exercise states of local muscles, it is difficult to accurately determine an exercise state of a user and to provide effective exercise guidance for the user; and on the other hand, there is a higher cost for exercise guided by a personal trainer, while the exercise monitoring device can lead to inconvenience of doing exercise for the user.

It should be noted that information disclosed by the foregoing technical background is only intended to further understand the background of the present disclosure, and therefore can include information that does not constitute related technology already known by those ordinary skill in the art.

SUMMARY

According to one aspect of the present disclosure, an exercise guidance method is provided, which includes receiving myoelectric parameters of a user collected by a plurality of myoelectric sensors, determining a current exercise state of the user based on said myoelectric parameters, generating exercise guidance information based on the current exercise state, and sending the exercise guidance information to a terminal.

In an exemplary arrangement of the present disclosure, a plurality of flexible electrodes are provided at a plurality of body parts of the user, collecting myoelectric parameters of the plurality of body parts of the user.

In an exemplary arrangement of the present disclosure, after receiving myoelectric parameters of a user collected by a plurality of myoelectric sensors, the method further includes reconstituting and denoising said myoelectric parameters by wavelet transform method.

In an exemplary arrangement of the present disclosure, said myoelectric parameters includes muscle fatigue levels and muscle excitement levels.

In an exemplary arrangement of the present disclosure, determining a current exercise state of the user based on myoelectric parameters includes calculating a plurality of time-frequency parameters corresponding to said myoelectric parameters and evaluating the muscle fatigue levels and the muscle excitement levels of the body parts respectively corresponding to said myoelectric sensors using a vector machine algorithm based on the calculated time-frequency parameters, so as to determine the current muscle state of the user.

In an exemplary arrangement of the present disclosure, the above method further includes: obtaining a muscle state index of the user based on body parameters and the determined current muscle state of the user, and storing a standard myoelectricity for various exercise states and a range of the muscle state index corresponding to different exercise states in a database.

Optionally, the muscle state index can range from 0 to 1.

In an exemplary arrangement of the present disclosure, generating an exercise guidance information based on the current exercise state includes comparing the current muscle state index and a standard muscle state index and generating the exercise guidance information according to a result of the comparison.

In an exemplary arrangement of the present disclosure, generating exercise guidance information based on the current exercise state includes determining a current exercise motion to be not standard and generating the exercise guidance information that prompts the user to adjust the current exercise motion in response to determining that a difference between the muscle state index of the current exercise motion and the muscle state index of the standard motion is larger than an allowable error, otherwise, determining the current exercise motion to be standard and generating the exercise guidance information with praise or encouragement.

In an exemplary arrangement of the present disclosure, the method further includes setting a prompt message so that the terminal prompts the user to adjust the current exercise motion.

In an exemplary arrangement of the present disclosure, the method further includes arranging the plurality of myoelectric sensors on a wearable device.

In an exemplary arrangement of the present disclosure, the time-frequency parameter includes one or more of an absolute value integral, a variance, a root mean square amplitude, an amplitude, a zero crossing point and a median frequency.

According to one aspect of the present disclosure, an exercise guidance device is provided, which includes a myoelectric parameter receiving sub-circuit, configured to receive myoelectric parameters of a user collected by a plurality of myoelectric sensors, an exercise state determining sub-circuit, configured to determine a current exercise state of the user based on myoelectric parameters, a guidance information generating sub-circuit, configured to generate exercise guidance information based on the current exercise condition, and to send the exercise guidance information to a terminal.

In an exemplary arrangement of the present disclosure, the device further includes a myoelectric parameters acquisition sub-circuit including the plurality of myoelectric sensors arranged on a wearable device.

In an exemplary arrangement of the present disclosure, said myoelectric parameters includes muscle fatigue levels and muscle excitement levels.

In an exemplary arrangement of the present disclosure, the exercise state determining sub-circuit is further configured to calculating a plurality of time-frequency parameters corresponding to said myoelectric parameters, and evaluating the muscle fatigue levels and the muscle excitement levels at the body parts respectively corresponding to said myoelectric sensors using a vector machine algorithm based on the calculated time-frequency parameters, so as to determine the current muscle state of the user.

In an exemplary arrangement of the present disclosure, the exercise state determining sub-circuit is further configured to obtain a muscle state index of the user based on body parameters and the determined current muscle state of the user, and store a standard myoelectricity for various exercise states and a range of the muscle state index corresponding to different exercise states in a database.

In an exemplary arrangement of the present disclosure, the muscle state index ranges from 0 to 1.

In an exemplary arrangement of the present disclosure, the guidance information generating sub-circuit is further configured to compare the current muscle state index and a standard muscle state index, and generate the exercise guidance information according to the comparison result.

In an exemplary arrangement of the present disclosure, the guidance information generating sub-circuit is further configured to determine a current exercise motion to be not standard and generate the exercise guidance information that prompts the user to adjust the current exercise motion in response to determining that a difference between the muscle state index of the current exercise motion and the muscle state index of the standard motion is larger than an allowable error, otherwise, determine the current exercise motion to be standard and generate the exercise guidance information with praise or encouragement.

In an exemplary arrangement of the present disclosure, the time-frequency parameter includes one or more of an absolute value integral, a variance, a root mean square amplitude, an amplitude, a zero crossing point and a median frequency.

BRIEF DESCRIPTION OF THE DRAWINGS

The accompanying drawings herein are incorporated in and constitute at least a part of this specification, illustrate arrangements consistent with the present disclosure, and serve to explain principles of the present disclosure together with the description. Obviously, the accompanying drawings in the following description are illustrated according to some arrangements of the present disclosure, and those skilled in the art can also obtain other drawings based on these drawings without any creative work.

DETAILED DESCRIPTION

Figure 1:
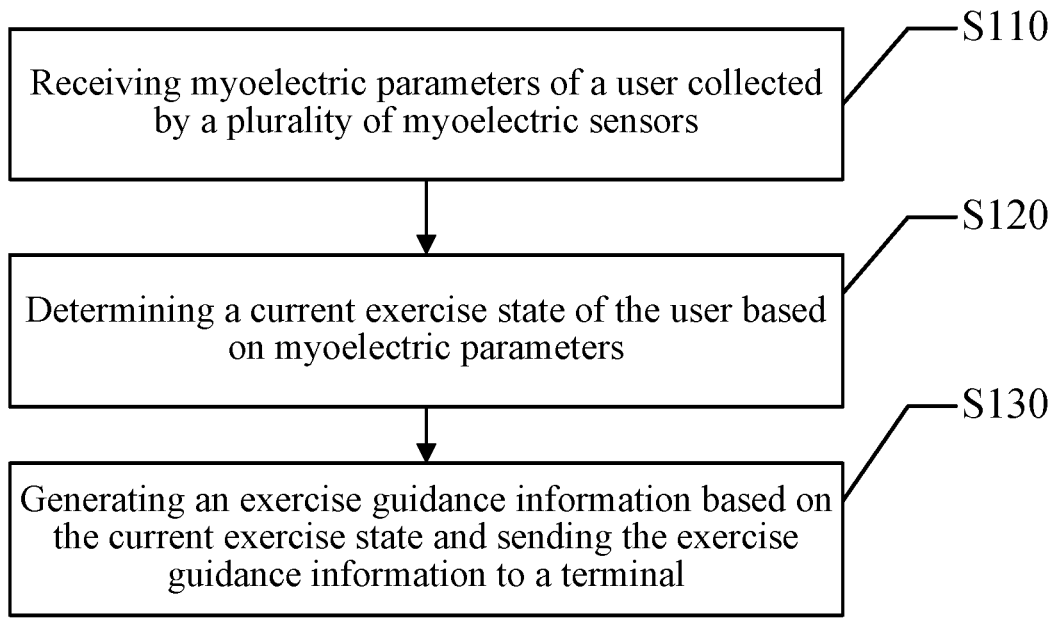
FIG. 1 schematically shows a schematic view of an exercise guidance method according to an exemplary arrangement of the present disclosure.

Example arrangements will now be described more fully with reference to the accompanying drawings. However, example arrangements can be implemented in various forms and should not be construed as limitation to examples set forth herein; on the contrary, various specific details are, configured to provide a thorough understanding of arrangements of the present disclosure. Features, structures or characteristics described can be combined in one or more arrangements in any suitable manner.

Moreover, drawings are schematic illustrations of the present disclosure and are not necessarily drawn in scale. The same reference numbers in the drawings denote the same or similar parts, of which repeated description will therefore be omitted. Some of block diagrams shown in these drawings are functional entities and do not necessarily have to correspond to physically or logically independent entities. There functional entities can be implemented in a software form, or can be implemented in one or more hardware sub-circuits or integrated circuits, or can be implemented in different network and/or processor devices and/or microcontroller devices.

In an exemplary arrangement, an exercise guidance method is firstly provided as shown in FIG. 1, the exercise guidance method can include the following blocks:

at block S110: receiving myoelectric parameters of a user collected by a plurality of myoelectric sensors;

at block S120: determining a current exercise state of the user based on myoelectric parameters;

at block S130: generating exercise guidance information based on the current exercise condition, and sending the exercise guidance information to a terminal.

The exercise guidance method according to an exemplary arrangement of the present disclosure can determine the current exercise state of the user based on myoelectric parameters of the user collected by the plurality of myoelectric sensors and generate the exercise guidance information. On one hand, a local muscle state of the user can be accurately reflected by the collected myoelectric parameters to achieve more accurate motion detection, and to provide more accurate exercise guidance during exercise. On the other hand, disadvantages of the exercise guidance method such as high cost and inconvenience to carry are avoided, thereby reducing cost and increasing convenience, and thus improving user experience.

Figure 2:
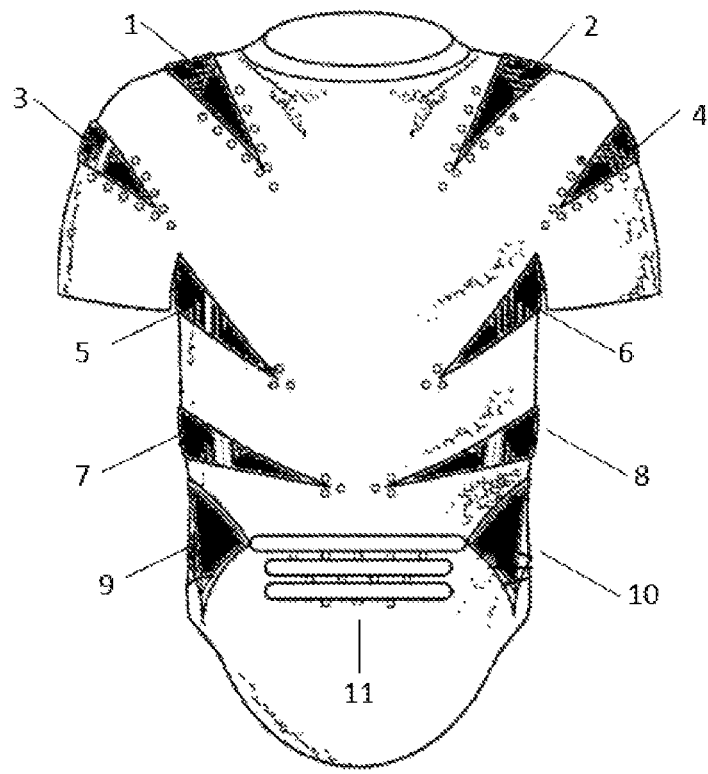
FIG. 2 schematically shows a positional schematic view of myoelectric sensors according to an exemplary arrangement of the present disclosure.
Figure 3:
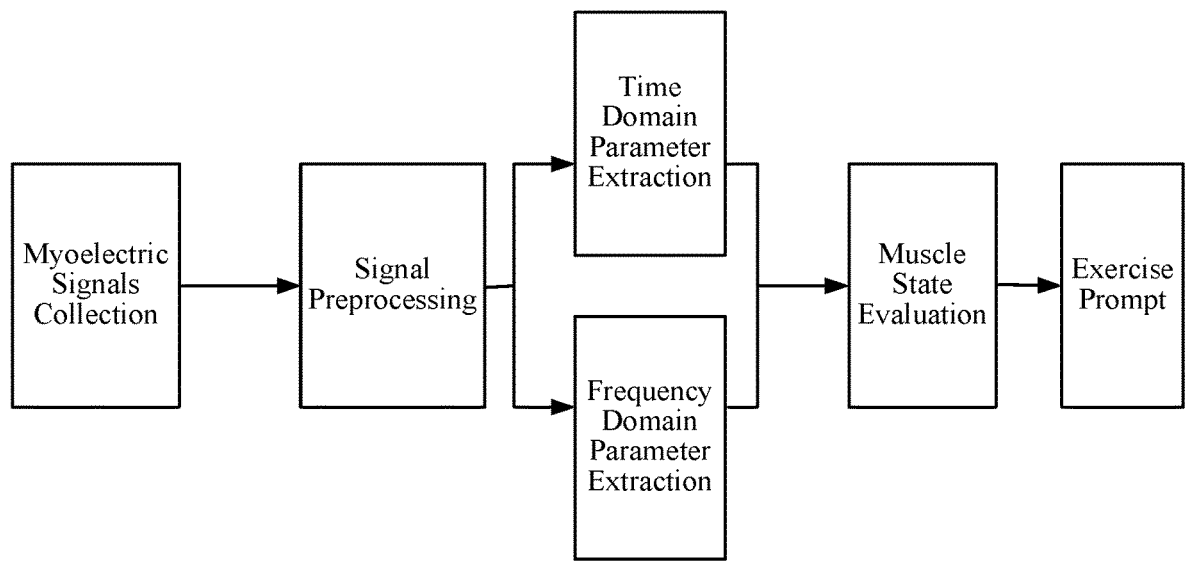
FIG. 3 schematically shows a data processing flowchart in an exercise guidance method according to an exemplary arrangement of the present disclosure.

Next, the exercise guidance method according to an exemplary arrangement will be described with reference to FIG. 2 to FIG. 4.

At block S110, myoelectric parameters of the user collected by a plurality of myoelectric sensors are received.

In an exemplary arrangement, the myoelectric sensor can include a flexible electrode. The plurality of myoelectric sensors can collect myoelectric parameters in different positions, with reference to FIG. 2, a plurality of flexible electrodes 1-10 can collect myoelectric signals in different parts such as arm, abdomen and waist, and acquire myoelectric parameters in different parts of the user through a multichannel myoelectric sensor in order to reflect muscle state to a certain extent.

In an exemplary arrangement, the method can further include: arranging the plurality of myoelectric sensors on a wearable device.

In an exemplary arrangement, the wearable device can be, for example, a close-fitting sportswear which can be used for monitoring exercise state of the user, the close-fitting sportswear can include a plurality of myoelectric sensors. The sensor can act as a flexible electrode. A novel flexible electrode material is used in the close-fitting sportswear instead of the conventional metal electrode, and the flexible electrode can be weaved into the sportswear. With reference to FIG. 2, the plurality of flexible electrodes can be provided at different positions of the sportswear to collect myoelectric parameters at different parts such as arm, abdomen and waist of the user, and to acquire myoelectric parameters in different parts of the user through a multichannel myoelectric sensor. After myoelectric signals are collected, the collected myoelectric signals can be analog-to digital converted and stored in a designated register. The myoelectric sensor is provided in the close-fitting sportswear so that it is more portable and more comfortable than traditional devices such as sports watches, and so that the current exercise state of the user can be accurately reflected through these myoelectric parameters.

In some arrangements, in order to eliminate interference of other signals on the collected myoelectric signals, after receiving myoelectric parameters of the user collected by a plurality of myoelectric sensors, the method can further include: reconstituting and denoising said myoelectric parameters by wavelet transform method.

In an exemplary arrangement, since the wavelet transform method is a local transformation between space or time and frequency and thus can perform multi-scale detailed analysis of frequency or signal with computing functions such as scaling and translation, information can be effectively extracted from the signal. For example, the myoelectric signal itself is a relatively weak signal with a general amplitude of 100-5000 uV. In this example, when signal collected with a sampling rate of 1000 Hz, frequency spectrum energy distribution of the myoelectric signal is between 50-150 Hz. Therefore, the collected myoelectric signal is firstly treated by using band-pass filtering of 50-150 Hz, completely decomposed through 4 layers using sym 8 wavelet to denoise the myoelectric signal, and then the denoised myoelectric signal is obtained by wavelet reconstituting the lowest layer low frequency coefficient obtained by decomposing the wavelet and high frequencies at various layers. In this example, decomposition and denoising process of the wavelet can be implemented by, for example, Matlab program.

At block S120, a current exercise state of the user is determined based on myoelectric parameters.

In an exemplary arrangement, the muscle state of the user can be reflected by the current myoelectric signal received in the foregoing block S110. The muscle fatigue level and the muscle excitement level can be included. Thus, the current exercise state of the user can be determined based on the muscle state, for example, it can be determined whether the user doing sports is tired or not.

It should be noted that the standard exercise state can be determined based on the exercise type set by the user and exercise intensity. Since the type of exercise, exercise intensity, endurance and the like are different for users with different myoelectric parameters, the current exercise state of the user can also be determined in combination with basic myoelectric parameters such as gender information, limb joint health, spine health and blood glucose level. For example, the exercise type can include plank, sit-up and the like. The exercise intensity can be represented in the form with intervals.

The exercise type and the exercise intensity can be set on the terminal or an exercise detection device. For example, if the exercise detection device mentioned above has an input interface, the user can directly input the type of exercise, the exercise intensity and basic myoelectric parameters from the input interface (touch screen or keyboard). If the exercise detection device is able to receive voice information or short message information, the user can input his/her type of exercise, exercise intensity and basic physical parameters through voice or short message. Of course, the exercise detection device can also receive information in other ways, so that the user only needs to operate according to an input mode available.

Determining a current exercise state of the user based on myoelectric parameters can include:
calculating a plurality of time-frequency parameters corresponding to said myoelectric parameters;
determining a current muscle state of the user by various time-frequency parameters using vector machine algorithm.

In an exemplary arrangement, a plurality of time-frequency parameters corresponding to myoelectric signals are firstly calculated. The plurality of time-frequency parameters can include one or more of an absolute value integral, a variance, a root mean square amplitude, an amplitude, a zero crossing point and a median frequency, so that the calculated time-frequency parameters can be analyzed and optimized to perform evaluation of the current muscle state such as muscle fatigue level and vitality. The time-frequency parameter herein includes time domain parameters such as absolute value integration, variance, root mean square amplitude, amplitude, and frequency domain parameters such as zero crossing point and the median frequency. It should be noted that all subsequent calculations are based on myoelectric signals after wavelet denoised.

The denoised myoelectric signals are used to extract the corresponding time-frequency parameters, an exemplary calculation of each of time-frequency parameters is as follows:
calculating the absolute value integral (IAV) according to equation (1):

$$IAV = \frac{1}{N}\sum_{i=1}^{N} |x_i| \qquad \text{equation (1)}$$

calculating the zero crossing point (ZC) according to equation (2), where the zero crossing point is mainly used to reflect the relationship between the intensity of the myoelectric signal and the frequency of the electrical pulse:

$$ZC = \sum_{i=1}^{N} \text{sgn}(-x_i, x_{i+1}), \text{sgn}(x) = \begin{cases} 1 & \text{if } x > 0 \\ 0 & \text{otherwise} \end{cases} \qquad \text{equation (2)}$$

calculating the variance according to equation (3):

$$VAR = \frac{1}{N-1}\sum_{i=1}^{N} x_i^2 \qquad \text{equation (3)}$$

calculating the Willison amplitude (WAMP) according to equation (4) to mainly calculate the number of changes in the EMG amplitude:

$$WAMP = \sum_{i=1}^{N} f|x_i - x_{i+1}|, \quad f(x) = \begin{cases} 1 & \text{if } x > \text{threshold} \\ 0 & \text{otherwise} \end{cases} \quad \text{equation (4)}$$

calculating the root mean square amplitude (RMS) according to equation (5) to mainly describe an average change of myoelectricity over a certain period of time. The time that muscle fatigue occurred and fatigue level can be determined by comparing the root mean square amplitudes at different periods:

$$\text{RMS} = \sqrt{\frac{1}{N} \sum_{k=1}^{N} x_k^2} \quad \text{equation (5)}$$

calculating the median frequency (MF) or average power frequency (MPF) according to equation (6) to mainly reflect muscle disease and fatigue level through the frequency:

$$MPF = \frac{\int_0^{+\infty} f P(f) df}{\int_0^{+\infty} P(f) df} \quad \text{equation (6)}$$

In the foregoing equations, xi is the amplitude of the myoelectric signal collected at different times, and P(f) is a function of power spectral density of the myoelectric signal.

Due to randomness of the myoelectric signal and complexity of multiple factors, parameters such as the fatigue level associated with muscle status also depend on a variety of factors and cannot be evaluated using a single parameter. In order to solve the above problem, in the present exemplary arrangement, a set of myoelectric parameters are comprehensively combined by mapping analysis of a support vector machine so as to obtain a multivariate function to reflect the muscle state.

In this example, a vector machine regression algorithm can be used to iteratively compute pre-stored samples to adjust the mapping function. The mapping function can be in the form of a network structure. During evaluation of the muscle state with multi-layer perceptron network, the input is preferred in the above-mentioned calculated time-frequency parameters. Assuming that the number x of time-frequency parameters are used, the corresponding muscle evaluation function f(v) can be represented as equation (7):

$$f(v) = \frac{1}{1 + e^{-\left\{\sum_{1}^{N}\left(\frac{2}{1+e^{-2\left(v * w_n^{(1)T} + b_n\right)}}\right) * w_n^{(2)} + b_0\right\}}} \quad \text{equation (7)}$$

where v is a vector group of x*1, that is, a corresponding time-frequency parameter, $w_n^{(1)}$ is a weight vector of the number n of neurons corresponding to the first layer that trained by a vector machine, $w_n^{(2)}$ is a weight vector of the number n of neurons corresponding to the second layer, b0, b1, b2, bn are respectively corresponding deviation constants. The corresponding weight vector is iteratively updated by the support vector machine by using the pre-stored samples and the corresponding muscle states, so that an optimal mapping function of the muscle state index can be finally obtained.

The current muscle state of the corresponding user can be obtained according to f(v). The muscle state can be represented by the muscle state index, and muscle excitement level and fatigue level of the corresponding part can be obtained by this index.

At block S130, exercise guidance information is generated based on the current exercise condition, and the exercise guidance information is sent to a terminal.

In an exemplary arrangement, the current exercise state can be described by the current muscle state index and the current exercise motion. The exercise guidance information corresponding to the current exercise state can be generated based on the current exercise state determined in the block S120 described above. For example, guidance information can be generated to prompt the user to rest or reduce the exercise intensity when the muscle fatigue determined; and information with praise or encouragement can be generated in response to determining that it is determined that the exercise state of the user is qualified. The exercise guidance information can include text prompt information, and can also include sound or light prompt information. The wearable device in this example can send information to the terminal in a wireless or wired manner. For example, the exercise guidance information can be directly transmitted to the terminal through a wireless network (a computer network, a mobile communication network (such as a metropolitan area network, a wide area network, a local area network (such as: Bluetooth), etc.).

In an exemplary arrangement, the terminal can receive the exercise guidance information generated by the above method and display the exercise guidance information to achieve detailed guidance on the exercise state of the user. With regard to the user, as long as the terminal is within the range that the user can see or perceive, the user can be guided to perform reasonable exercise or effective exercise according to the generated exercise guidance information.

In this example, generating exercise guidance information based on the current exercise state can include:

determine whether the current muscle state and a standard muscle state are matched;

generating the exercise guidance information corresponding to the matched result.

In an exemplary arrangement, the exercise guidance information can be generated according to size of the calculated current muscle state index. The muscle state index can reflect muscle fatigue level and excitability. The user is divided into different types according to body mass index (BMI), body fat content, age and gender, a certain number of people in each type being selected as a sample to collect myoelectric signals for different exercise states so that the corresponding muscle excitement level and fatigue level are defined according to a range of muscle state index f(v) relative to various exercise states of the sample after training the sample to obtain the muscle state index f(v), and a standard myoelectricity for various exercise states and the range of the muscle state index f(v) corresponding to different exercise states being stored in a database.

Figure 4:
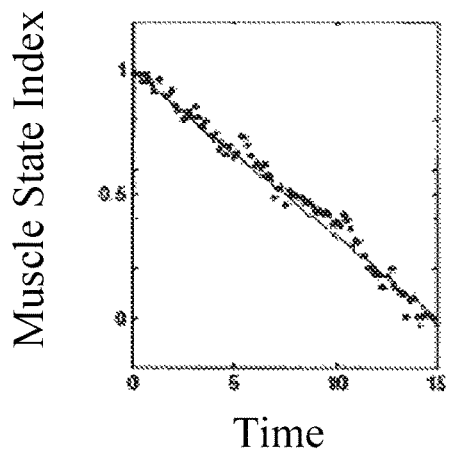
FIG. 4 schematically shows a schematic view of muscle state exponential values corresponding to different exercise states according to an exemplary arrangement of the present disclosure.
Figure 5:
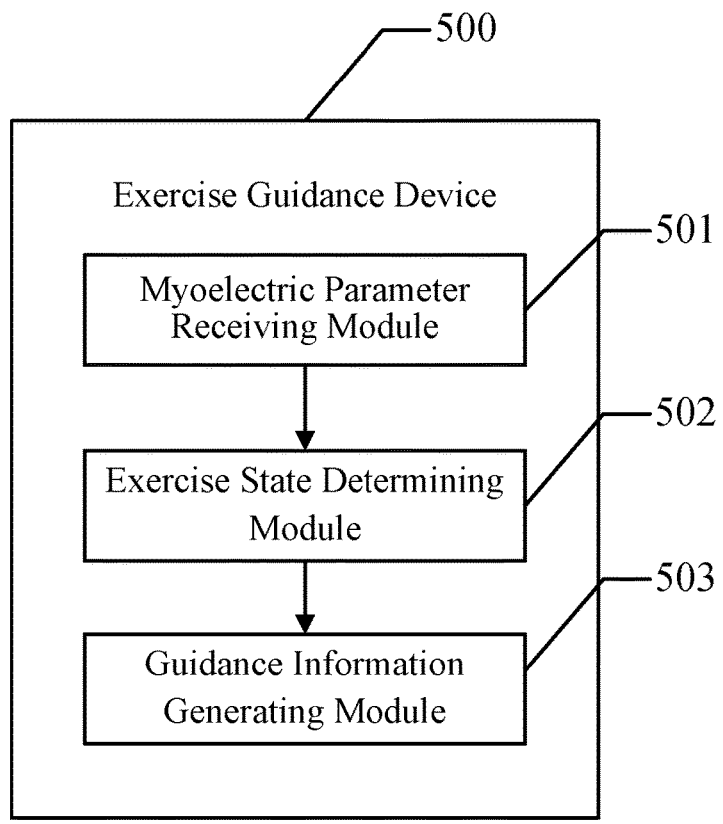
FIG. 5 schematically shows a block diagram of an exercise guidance device according to an exemplary arrangement of the present disclosure.

With reference to FIG. 4, values of the muscle state index corresponding to the sample shown in different exercise states are shown, so that the value of f(v) can be used to represent different muscle states. For example, f(v) corresponds to a value between 0 and 1. When f(v) is 1, the user's muscle is in a non-fatigue state; when f(v) approaches 0, it indicates that the muscle is in a state of complete fatigue and cannot complete the corresponding exercise. The muscle state index showing muscle fatigue level approaches a linear relationship under the same exercise intensity.

When used by the user, the value of f(v) can be calculated in real time according to the collected myoelectric signal of various parts. Then, by judging the range of the value, muscle fatigue level and excitability in various parts and exercise effect of different parts can be known. The result is fed back to the user in real time, thereby providing the user with feasible exercise guidance information and exercise arrangement. For example, the exercise guidance information can be generated to prompt the user to rest for a preset time or to prompt the user to reduce the exercise intensity when f(v) approaches 0. When f(v) is 1, it is possible to generate exercise guidance information that prompts the user to increase the exercise intensity. In this example, the collected myoelectric parameters can accurately reflect the local muscle state of the user, achieve more accurate exercise detection, and provide the user with more refined exercise guidance during exercise.

In addition, in this example, generating exercise guidance information based on the current exercise state can further include:

comparing the current muscle state index and a standard muscle state index to detect whether the current exercise motion is standard;

generating the exercise guidance information corresponding to a detection result.

In an exemplary arrangement, it is also possible to compare the current exercise motion relative to the exercise type and the exercise intensity that is preset and the standard exercise motion stored in the device in order to determine or detect whether the current exercise motion is standard, so that the corresponding exercise guidance information is generated according to the result. Determining whether the action is standard herein can allow a preset error between the current exercise motion and the standard exercise motion stored in the device. For example, the current exercise motion is determined to be not standard in response to determining that a difference between the muscle state index of the current exercise motion and the muscle state index of the standard motion is larger than an allowable error so as to prompt the user to adjust the current exercise motion and to guide how to adjust the action (for example, by video or slow-exercise guidance). Otherwise, the current exercise motion of the user is determined to be standard so as to generate the exercise guidance information with praise or encouragement. The current exercise motion of the user can be automatically determined whether it is standard and the corresponding guidance information can be generated by the method in this example, thereby avoiding the user's dependence on the personal fitness trainer in the related technology and reducing cost. In addition, with respect to exercise motion detection using a camera, the detection accuracy is higher and more detailed and comprehensive guidance can be provided.

In another arrangement, the muscle state index of different body parts can be calculated according to the myoelectric parameters collected by the electrodes of different body parts, and the local exercise guidance information can be provided by comparing the muscle state index of the corresponding body part with the standard motion, thereby improving user experience.

Optionally, in this exemplary arrangement, the method can further include:

setting a prompt message so that the terminal prompts the user to adjust the current exercise motion.

In an exemplary arrangement, during exercise of the user, a prompt message can be sent to the terminal, so that the terminal prompts the user to adjust its own exercise condition. The terminal can directly send the state prompt information to the user, which can be in the form of a short message or voice or other form that enables the user to obtain information. When the user receives this state prompt message during exercise, he/she can be able to adjust his/her own motion to avoid damage caused by excessive exercise intensity, or to avoid lack of exercise intensity which can not achieve the purpose of sports. Of course, the processor can also directly send state prompt information to the terminal. The status prompt information can be prompt information for slowing down the motion rhythm, and the terminal can directly notify the user of the status prompt information, and the user adjusts exercise state according to the prompt information. The terminal herein can be a smart terminal such as a mobile phone, a PAD, or the like. The prompt information can be used for real-time feedback on the user's exercise condition, thereby providing the user with fine exercise guidance.

In addition, in the present exemplary arrangement, an exercise guidance device 500 is also provided. The exercise guidance device 500 can further include:

a myoelectric parameter receiving sub-circuit 501, configured to receive myoelectric parameters of a user collected by a plurality of myoelectric sensors;

an exercise state determining sub-circuit 502, configured to determine a current exercise state of the user based on myoelectric parameters;

a guidance information generating sub-circuit 503, configured to generate exercise guidance information based on the current exercise condition, and sending the exercise guidance information to a terminal.

In addition, in the present exemplary arrangement, the exercise guidance device 500 can further include: a myoelectric parameters acquisition sub-circuit including the plurality of myoelectric sensors arranged on a wearable device.

The details of the sub-circuits in the above-mentioned exercise guidance device have been described in detail in the corresponding exercise guidance methods, and therefore will not be described here.

Figure 6:
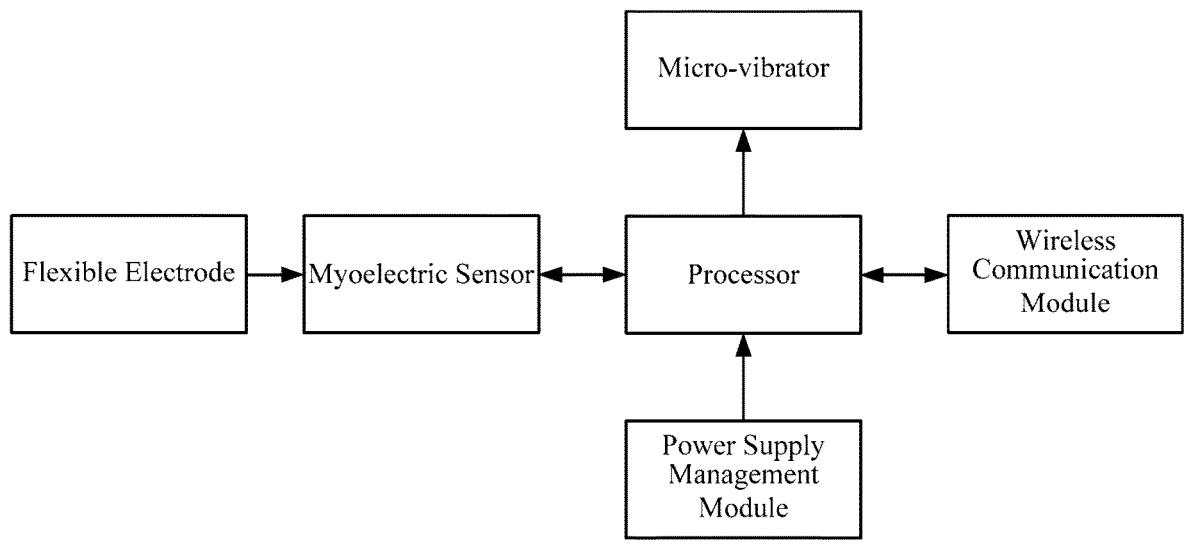
FIG. 6 schematically shows a hardware block diagram of an exercise guidance device according to an exemplary arrangement of the present disclosure.

In the present exemplary arrangement, in addition to the above sub-circuit, the exercise guidance device can further include: a micro-vibrator configured to feed back the generated prompt information to the user. The exercise guidance device can be applied in the close-fitting sportswear as shown in FIG. 2, and its hardware composition is shown in FIG. 6. It is mainly composed of a flexible electrode, a myoelectric sensor, a processor, a wireless communication sub-circuit, a micro-vibrator and a power supply. These sub-circuits are arranged in the position where the reference numeral 11 is located in the close-fitting sportswear. The power supply is powered by the Li battery; the processor is a 32-bit low-power ARM processor, which can achieve signal acquisition control and signal processing; the wireless communication sub-circuit can send the generated exercise guidance information to the smart terminal through wireless transmission for display and storage. For example, it can directly send exercise guidance information to the terminal through WIFI, Bluetooth, etc. to provide the user with detailed exercise guidance advice function.

It should be noted that although several sub-circuits or units of the device for action execution are mentioned in the above detailed description, this division is not mandatory. In fact, according to arrangements of the present disclosure, the features and functions of the two or more sub-circuits or units described above can be implemented in one sub-circuit or unit. Conversely, the features and functions of one sub-circuit or unit described above can be divided into multiple sub-circuits or units.

Moreover, although various steps or blocks of the method in the present disclosure have been described in a specific order in the drawings, this does not require or imply that these steps must be performed in this particular order, or all illustrated steps must be performed to achieve the desired result. Additionally or alternatively, some steps can be omitted, multiple steps can be combined into one step, and/or one step can be broken down into multiple sub-steps.

Those skilled in the art will readily recognize other arrangements of the present disclosure upon consideration of the specification and practice of the disclosure disclosed herein. This application is intended to cover any variations, uses, or adaptations of the present disclosure which follow the general principles of the present disclosure and include any common knowledge or conventional techniques in this technical field not disclosed by the present disclosure. The description and examples are to be considered exemplary only, with the true scope and spirit of the disclosure being indicated by the appended claims.

What is claimed is:

1. An exercise guidance method, comprising:
receiving myoelectric parameters for a plurality of body parts of a user collected by a plurality of myoelectric sensors and a plurality of flexible electrodes provided at the body parts of the user;
after receiving the myoelectric parameters of the user collected by the plurality of myoelectric sensors, reconstituting and denoising the myoelectric parameters using a wavelet transform method, wherein the myoelectric parameters comprise muscle fatigue levels and muscle excitement levels;
determining a current exercise state of the user based on said myoelectric parameters by: calculating a plurality of time-frequency parameters corresponding to the myoelectric parameters, and determining a current muscle state of the user by evaluating the muscle fatigue levels and the muscle excitement levels of the body parts respectively corresponding to the myoelectric sensors using a vector machine algorithm based on the calculated time-frequency parameters, wherein the current exercise state of the user is further determined in combination with gender information, limb joint health, spine health, and blood glucose level of the user; and
generating exercise guidance information based on the current exercise state and sending the exercise guidance information to a terminal, wherein generating the exercise guidance information based on the current exercise state comprises determining whether the current muscle state of the user being represented by a muscle state index and a standard muscle state being represented by a standard muscle state index are matched, and generating the exercise guidance information corresponding to a matching result;
wherein the standard muscle state index is obtained by: dividing users into different types according to body mass index, body fat content, age, and gender of the users; selecting a number of people in each of the types as samples to collect the myoelectric parameters for different exercise states of the people; and training the samples.

2. The exercise guidance method according to claim 1, further comprising storing a standard myoelectricity for various exercise states and a range of the muscle state index corresponding to different exercise states in a database.

3. The exercise guidance method according to claim 2, wherein the muscle state index ranges from 0 to 1.

4. The exercise guidance method according to claim 3, wherein generating the exercise guidance information based on the current exercise state comprises:
in response to determining a difference between the muscle state index of the current exercise motion and the muscle state index of the standard motion is larger than an allowable error, determining a current exercise motion to be not standard and generating the exercise guidance information that prompts the user to adjust the current exercise motion; and
in response to determining the difference between the muscle state index of the current exercise motion and the muscle state index of the standard motion is not larger than an allowable error, determining the current exercise motion to be standard and generating the exercise guidance information with praise or encouragement.

5. The exercise guidance method according to claim 1, further comprising arranging the plurality of myoelectric sensors on a wearable device.

6. The exercise guidance method according to claim 1, wherein the time-frequency parameter comprises one or more of an absolute value integral, a variance, a root mean square amplitude, an amplitude, a zero crossing point, and a median frequency.

7. The exercise guidance method according to claim 1, wherein reconstituting and denoising the myoelectric parameters using the wavelet transform method comprises:
completely decomposing the myoelectric parameters through four layers using a sym 8 wavelet transform to denoise the myoelectric parameters; and
subsequently obtaining the denoised myoelectric parameters by wavelet reconstituting a lowest layer low frequency coefficient obtained by decomposing a wavelet and high frequencies at various layers.

8. The exercise guidance method according to claim 1, wherein the muscle state index, f(v), is determined by:

$$f(v) = \frac{1}{1+e^{-\left\{\sum_{1}^{N}\left(\frac{2}{1+e^{-2(v*w_n^{(1)T}+b_n)}}\right)*w_n^{(2)}+b_0\right\}}},$$

where v is a vector group of x*/ that is a corresponding time-frequency parameter, $w_n^{(1)}$ is a weight vector of a number n of neurons corresponding to a first layer that is trained by a vector machine, $w_n^{(2)}$ is a weight vector of a number n of neurons corresponding to a second layer that is trained by the vector machine, and $b_0$, $b_1$, $b_2$, $b_n$ are respectively corresponding deviation constants.

9. An exercise guidance device, comprising:
a myoelectric parameter receiving sub-circuit configured to receive myoelectric parameters of a plurality of body parts of a user collected by a plurality of myoelectric sensors and a plurality of flexible electrodes provided at the body parts of the user, wherein the myoelectric parameters are reconstituted and denoised using a wavelet transform method after receipt of the myoelectric parameters, the myoelectric parameters comprising muscle fatigue levels and muscle excitement levels;

an exercise state determining sub-circuit configured to determine a current exercise state of the user based on myoelectric parameters by:
calculating a plurality of time-frequency parameters corresponding to the myoelectric parameters; and
determining a current muscle state of the user by evaluating the muscle fatigue levels and the muscle excitement levels at the body parts respectively corresponding to the myoelectric sensors using a vector machine algorithm based on the calculated time-frequency parameter, wherein the current exercise state of the user is further determined in combination with gender information, limb joint health, spine health, and blood glucose level of the user; and
a guidance information generating sub-circuit configured to generate exercise guidance information based on the current exercise state, and to send the exercise guidance information to a terminal, wherein the exercise guidance information is generated based on the current exercise state by determining whether the current muscle state of the user being represented by a muscle state index and a standard muscle state being represented by a standard muscle state index are matched, and generating the exercise guidance information corresponding to a matching result;
wherein the standard muscle state index is obtained by:
dividing users into different types according to body mass index, body fat content, age, and gender of the users; selecting a number of people in each of the types as samples to collect the myoelectric parameters for different exercise states of the people; and training the samples.

10. The exercise guidance device according to claim 9, further comprising a myoelectric parameters acquisition sub-circuit comprising the plurality of myoelectric sensors arranged on a wearable device.

11. The exercise guidance device according to claim 9, wherein the exercise state determining sub-circuit is further configured to store a standard myoelectricity for various exercise states and a range of the muscle state index corresponding to different exercise states in a database.

12. The exercise guidance device according to claim 11, wherein the muscle state index ranges from 0 to 1.

13. The exercise guidance device according to claim 12, wherein the guidance information generating sub-circuit is further configured to:

in response to determining that a difference between the muscle state index of the current exercise motion and the muscle state index of the standard motion is larger than an allowable error, determine that a current exercise motion is not standard and generate the exercise guidance information that prompts the user to adjust the current exercise motion; and in response to determining that the difference between the muscle state index of the current exercise motion and the muscle state index of the standard motion is not larger than an allowable error, determine the current exercise motion to be standard and generate the exercise guidance information with praise or encouragement.

14. The exercise guidance device according to claim 9, wherein the time-frequency parameter comprises one or more of an absolute value integral, a variance, a root mean square amplitude, an amplitude, a zero crossing point, and a median frequency.

15. The exercise guidance device according to claim 9, wherein reconstituting and denoising the myoelectric parameters using the wavelet transform method comprises:
completely decomposing the myoelectric parameters through four layers using a sym 8 wavelet transform to denoise the myoelectric parameters; and
subsequently obtaining the denoised myoelectric parameters by wavelet reconstituting a lowest layer low frequency coefficient obtained by decomposing a wavelet and high frequencies at various layers.

16. The exercise guidance device according to claim 9, wherein the muscle state index, f(v), is determined by:

$$f(v) = \frac{1}{1+e^{-\left\{\sum_{1}^{N}\left(\frac{2}{1+e^{-2\left(v*w_n^{(1)}\right)^T+b_n}}\right)*w_n^{(2)}+b_0\right\}}},$$

where v is a vector group of x*/ that is a corresponding time-frequency parameter, $w_n^{(1)}$ is a weight vector of a number n of neurons corresponding to a first layer that is trained by a vector machine, $w_n^{(2)}$ is a weight vector of a number n of neurons corresponding to a second layer that is trained by the vector machine, and $b_0$, $b_1$, $b_2$, $b_n$ are respectively corresponding deviation constants.

* * * * *